(12) United States Patent
Matsuo et al.

(10) Patent No.: US 9,970,875 B2
(45) Date of Patent: May 15, 2018

(54) SENSOR CHIP FOR SPFS MEASUREMENT, SPFS MEASUREMENT METHOD USING SENSOR CHIP FOR SPFS MEASUREMENT, AND SPFS MEASUREMENT DEVICE EQUIPPED WITH SENSOR CHIP FOR SPFS MEASUREMENT

(71) Applicant: KONICA MINOLTA, INC., Tokyo (JP)

(72) Inventors: Masataka Matsuo, Hachioji (JP); Kenji Ishida, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 851 days.

(21) Appl. No.: 14/367,323

(22) PCT Filed: Dec. 25, 2012

(86) PCT No.: PCT/JP2012/083483
§ 371 (c)(1),
(2) Date: Jun. 20, 2014

(87) PCT Pub. No.: WO2013/099871
PCT Pub. Date: Jul. 4, 2013

(65) Prior Publication Data
US 2015/0011015 A1 Jan. 8, 2015

(30) Foreign Application Priority Data
Dec. 26, 2011 (JP) ................................. 2011-283962

(51) Int. Cl.
*G01N 33/551* (2006.01)
*G01N 21/64* (2006.01)
*G01N 33/543* (2006.01)

(52) U.S. Cl.
CPC ..... *G01N 21/648* (2013.01); *G01N 33/54373* (2013.01); *G01N 2021/6417* (2013.01)

(58) Field of Classification Search
CPC ................................................ G01N 33/54373
(Continued)

(56) References Cited

U.S. PATENT DOCUMENTS 6,707,622 B2    3/2004  Tominaga
8,477,312 B2 *  7/2013  Kimura ................ G01N 21/552
                                                    356/445

(Continued)

FOREIGN PATENT DOCUMENTS

EP    2189782 A2    5/2010
JP    2002048904 A  2/2002
(Continued)

OTHER PUBLICATIONS

Extended European Search Report issued in connection with the corresponding application No. EP12862962.3-1554/2799843, PCT/JP2012/083483; dated Jul. 22, 2015.
(Continued)

*Primary Examiner* — Chris L Chin
(74) *Attorney, Agent, or Firm* — Cantor Colburn LLP

(57) ABSTRACT

[Problem] To provide a sensor chip for SPFS measurement, by which, irrespective of environmental conditions, fluctuations are low in characteristics such as signal, noise, or detection sensitivity, quantitative property can be ensured, and a highly precise and accurate SPFS measurement can be carried out. [Solution] A sensor chip for SPFS measurement which has a dielectric member having been produced by carrying out injection molding of a resin, when viewing from the metal thin film-formed surface side of the dielectric member and taking as b the distance of the side end surface position of the resin inlet to the position on the metal thin
(Continued)

film-formed surface that is farthest from the side end surface position of the resin inlet, the center of a ligand immobilization part is located in the area between the 3b/8 position and the 6b/8 position from the side end surface position of the resin inlet.

11 Claims, 15 Drawing Sheets

(58) Field of Classification Search
USPC .................................................. 422/82.11
See application file for complete search history.

(56) References Cited

U.S. PATENT DOCUMENTS

| | | |
|---|---|---|
| 2002/0127706 A1 | 9/2002 | Naya et al. |
| 2006/0170918 A1 | 8/2006 | Nishiuma |
| 2008/0088847 A1 | 4/2008 | Muraishi et al. |
| 2010/0128274 A1 | 5/2010 | Kimura |
| 2010/0195107 A1 | 8/2010 | Naya et al. |

FOREIGN PATENT DOCUMENTS

| | | |
|---|---|---|
| JP | 2006208294 A | 8/2006 |
| JP | 2007248430 A | 9/2007 |
| JP | 2010210451 A | 9/2010 |
| JP | 4689907 B2 | 6/2011 |
| JP | 2011185698 A | 9/2011 |
| WO | 2011074373 A1 | 6/2011 |

OTHER PUBLICATIONS

International Search Report for the International application No. PCT/JP2012/083483, dated Mar. 19, 2013.

Written Opinion of the International Searching Authority for the International application No. PCT/JP2012/083483; dated Mar. 19, 2013. English translation attached.

European Office Action corresponding to Application No. 12862962.3-1554; dated Aug. 7, 2017.

* cited by examiner

[Fig. 1]
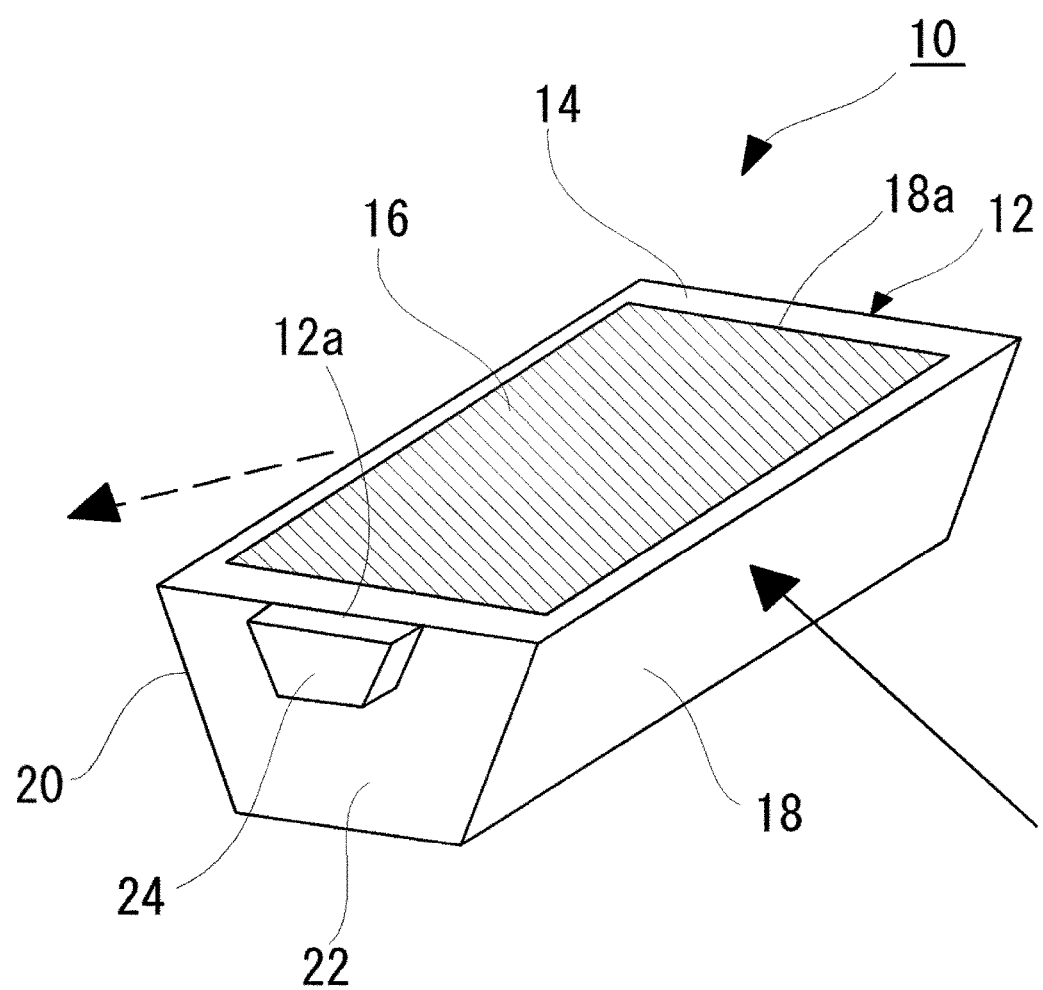

[Fig. 2]
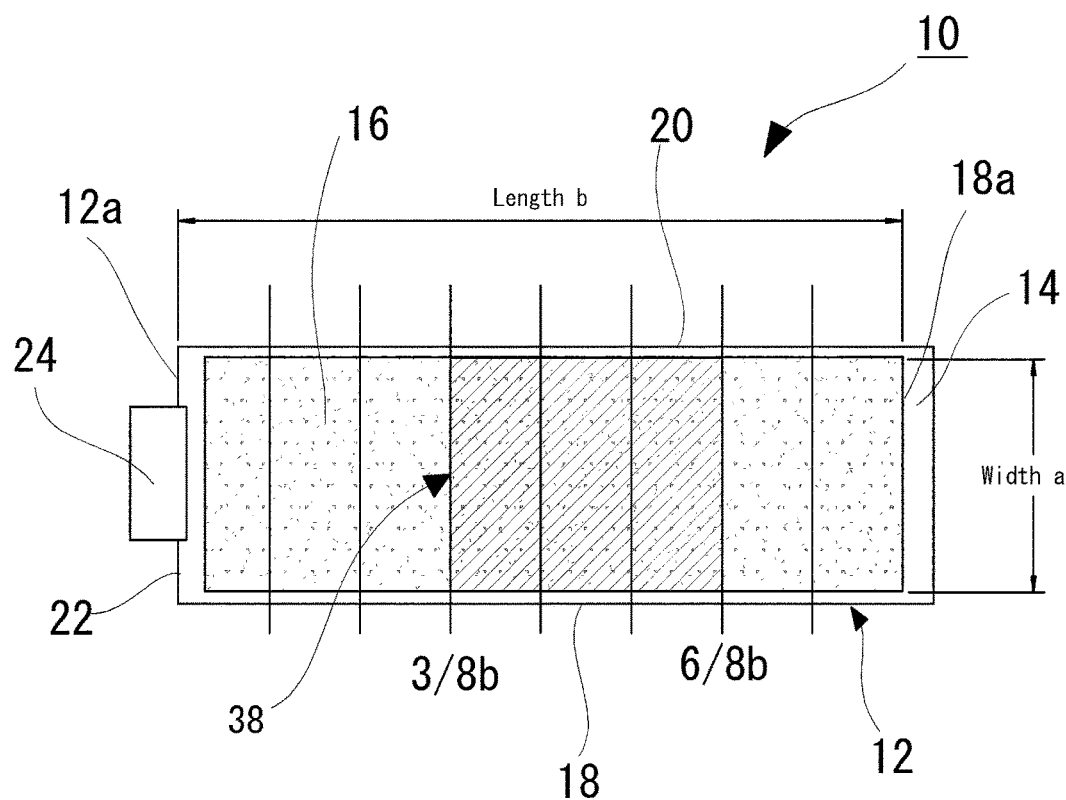

[Fig. 3]
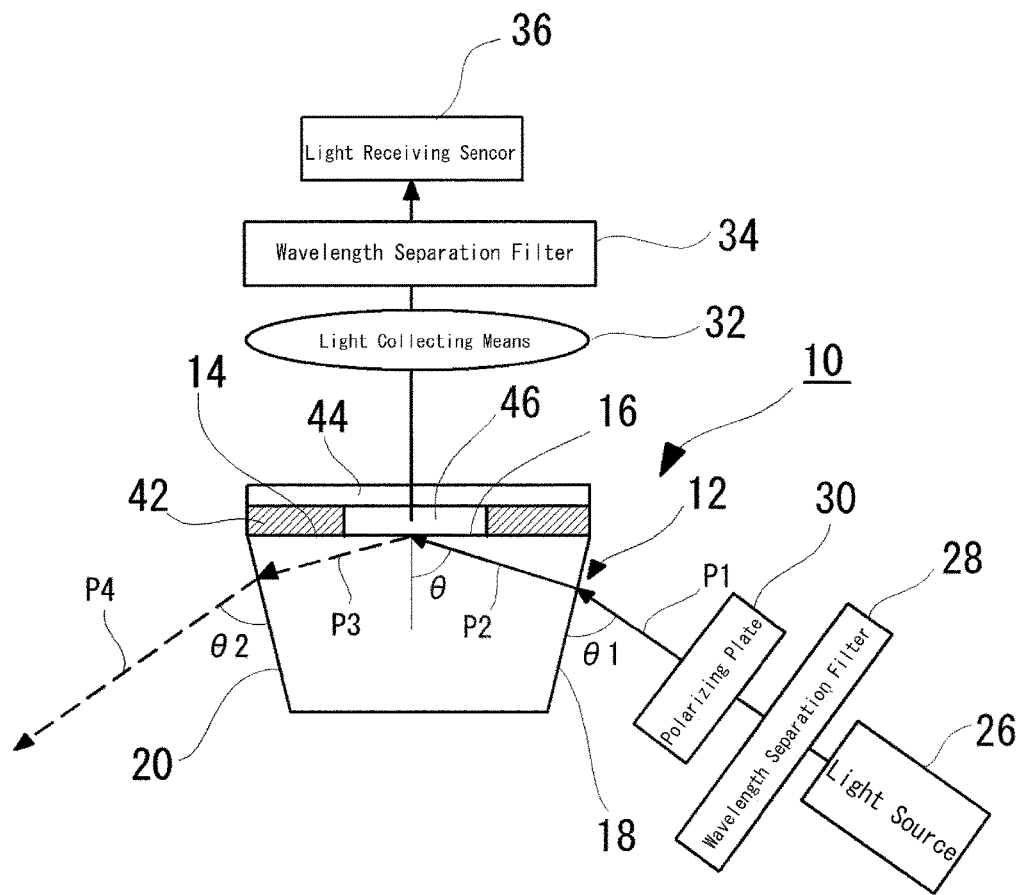

[Fig. 4]
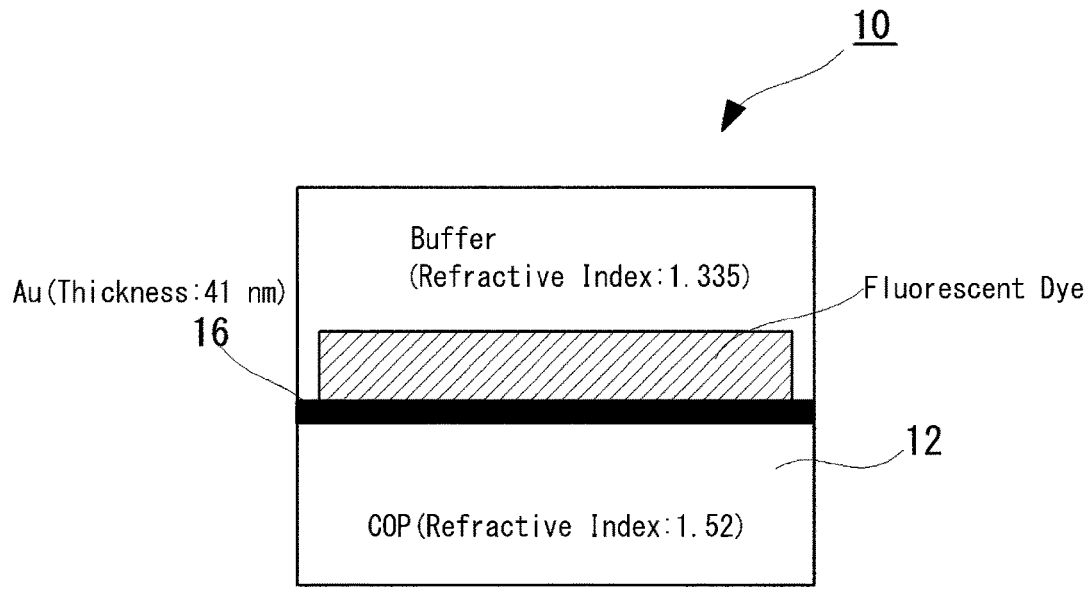
[Fig. 5]
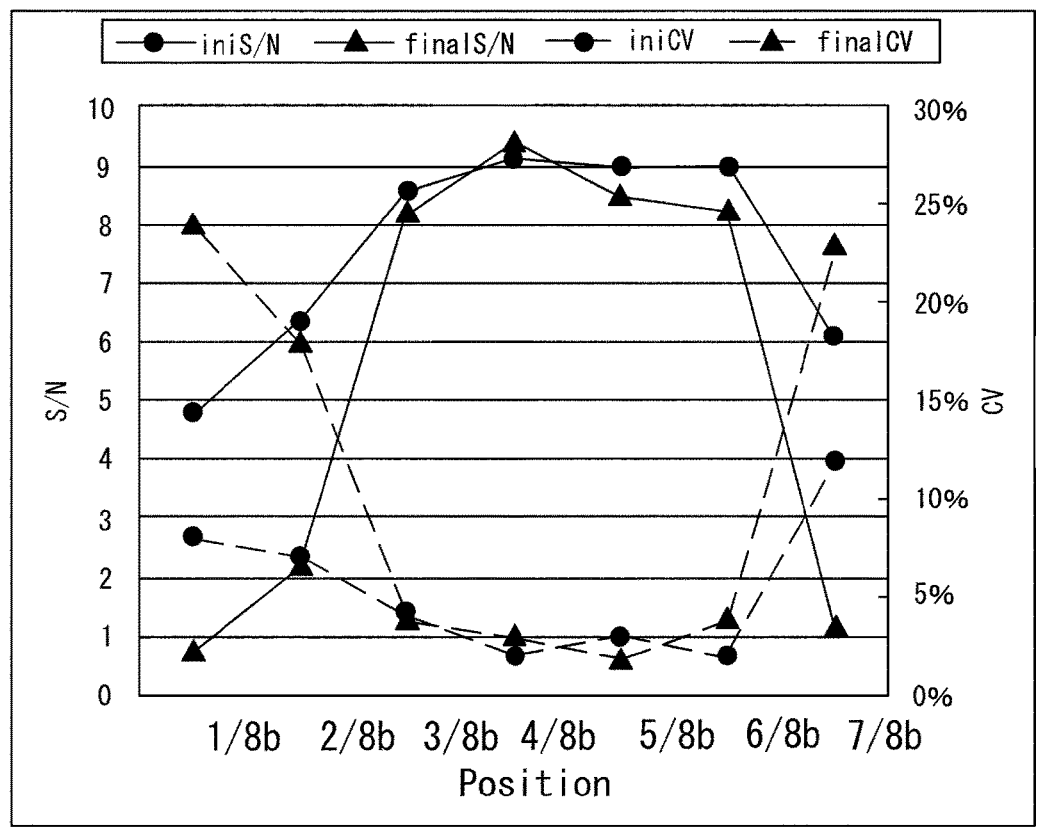

[Fig. 6]
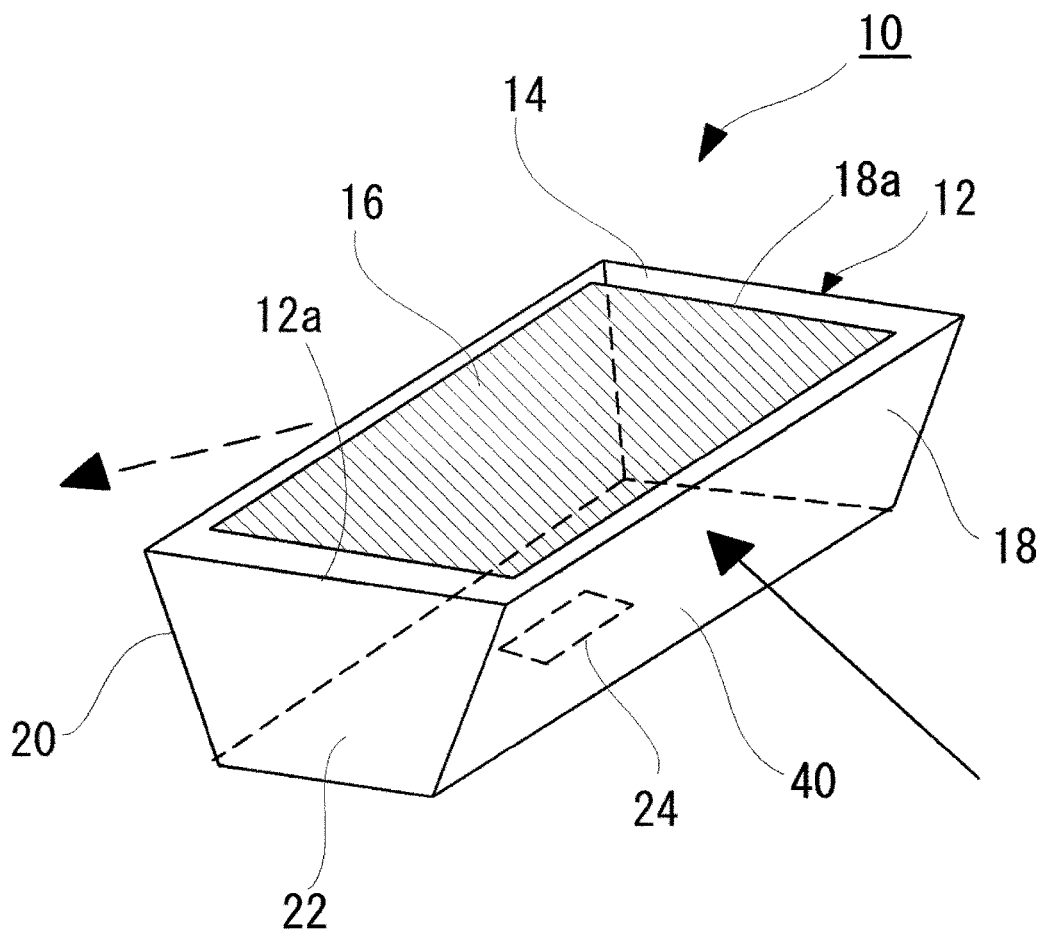

[Fig. 7]
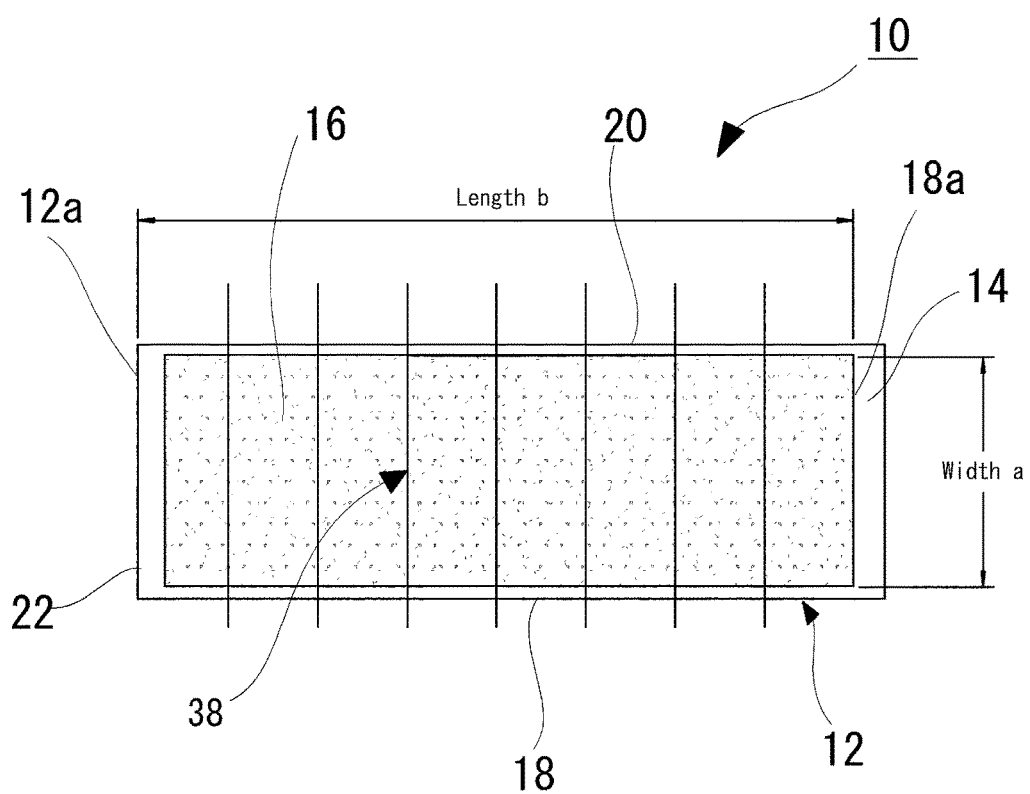

[Fig. 8]
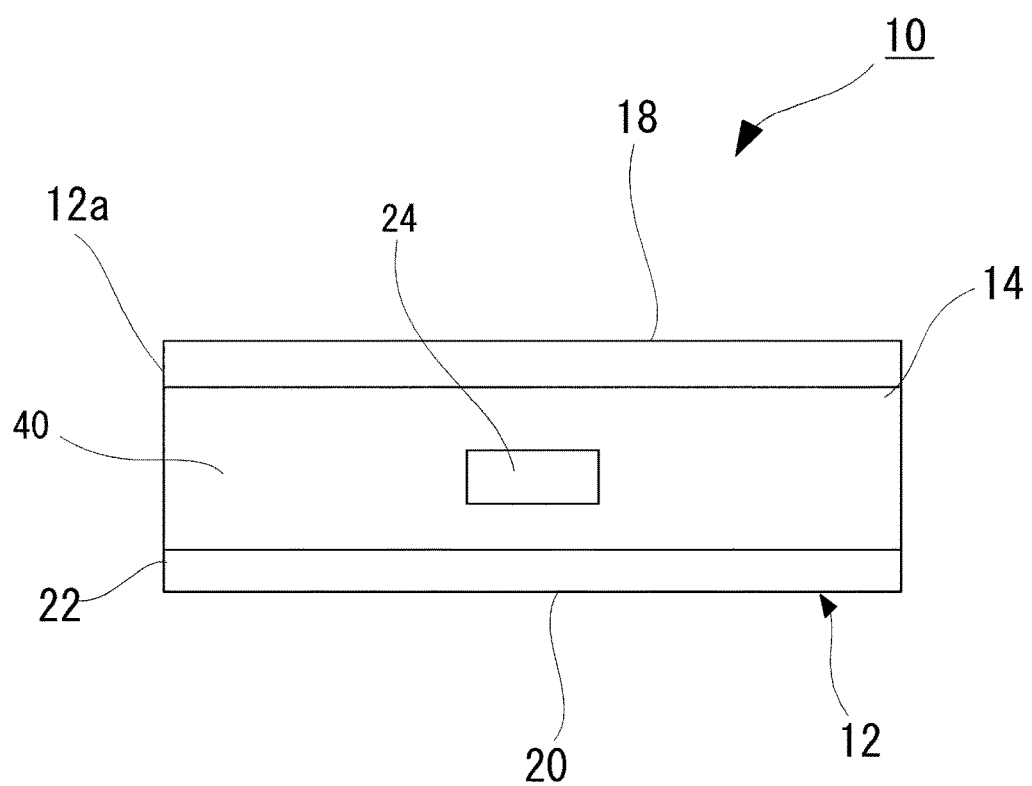

[Fig. 9]
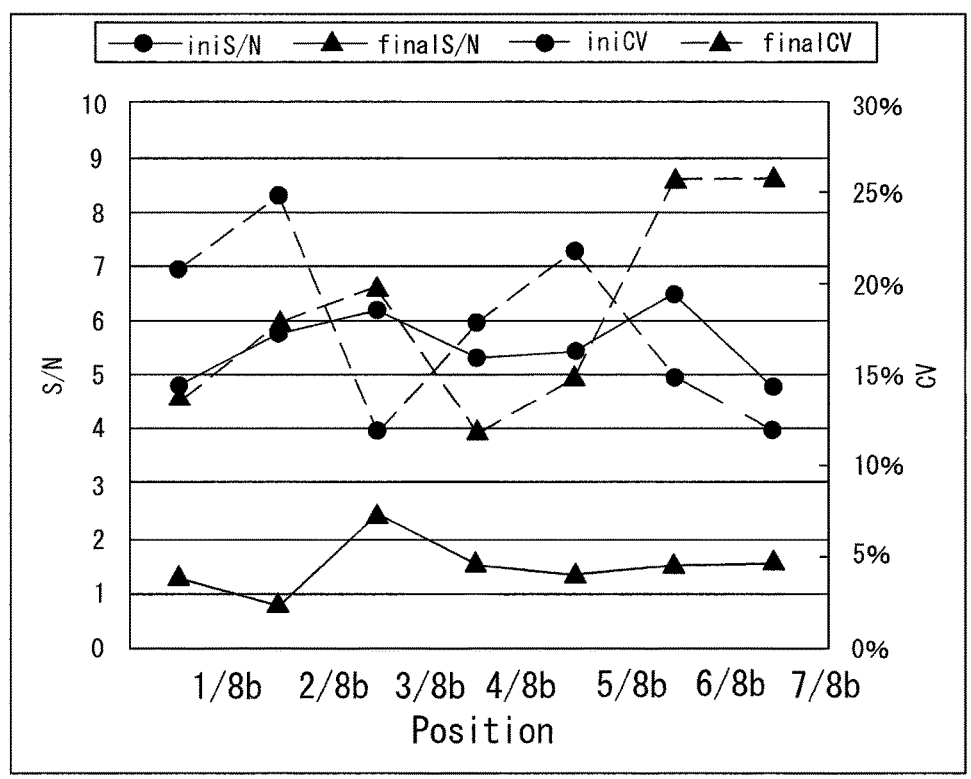

[Fig.10]
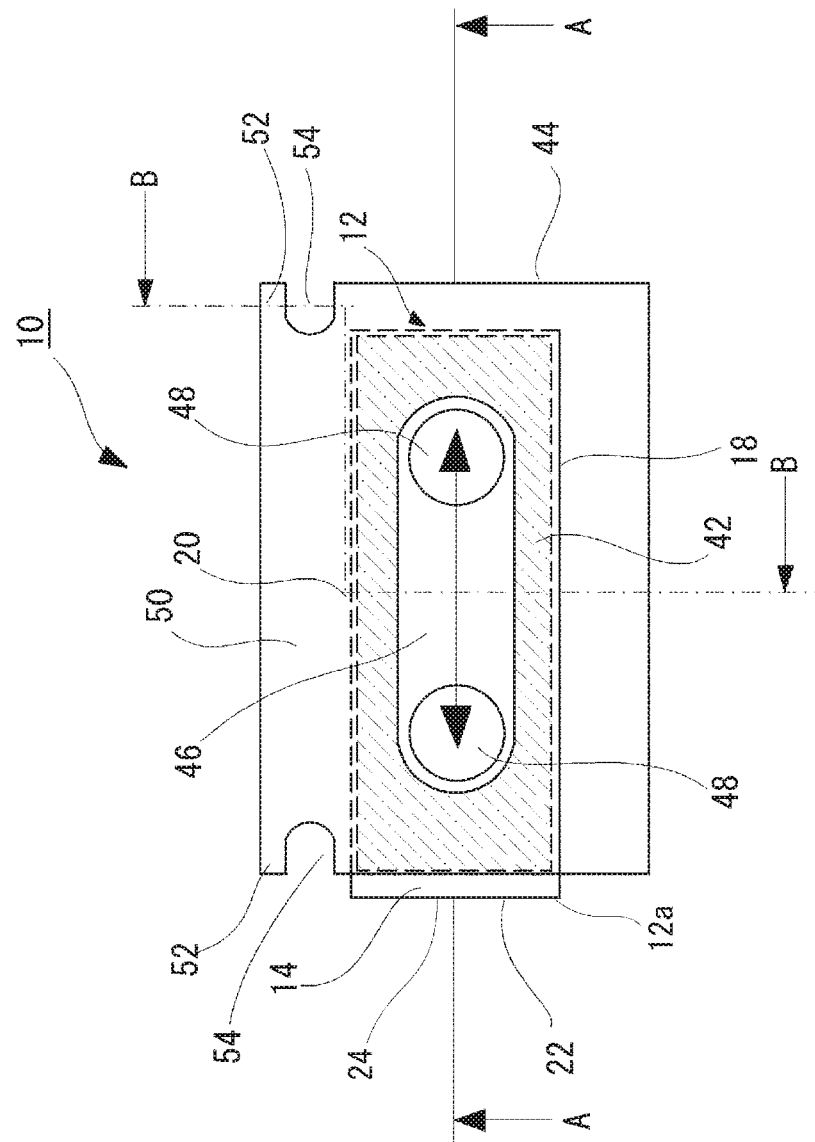

[Fig.11]
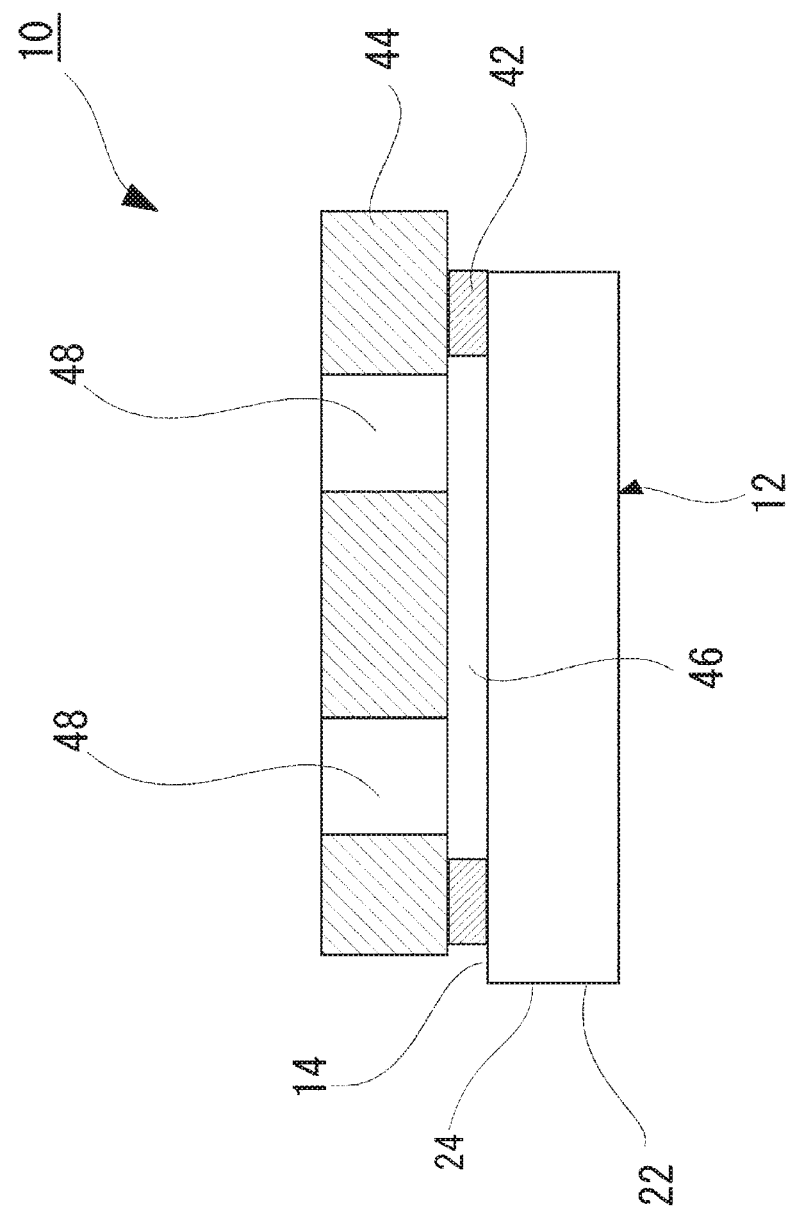

[Fig. 12]
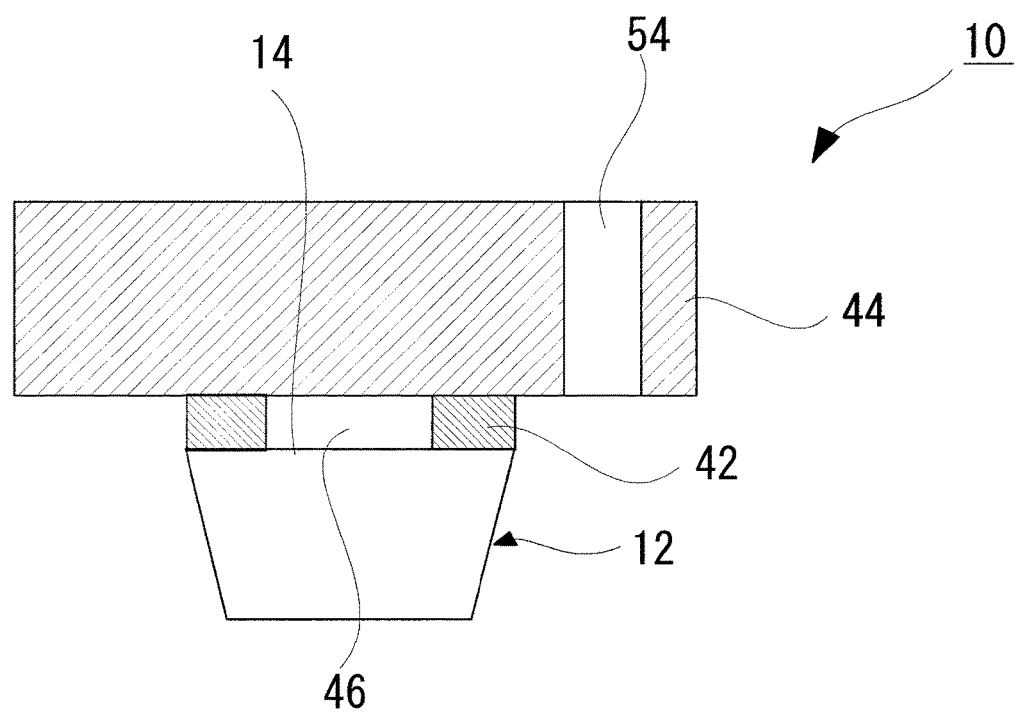

[Fig.13]
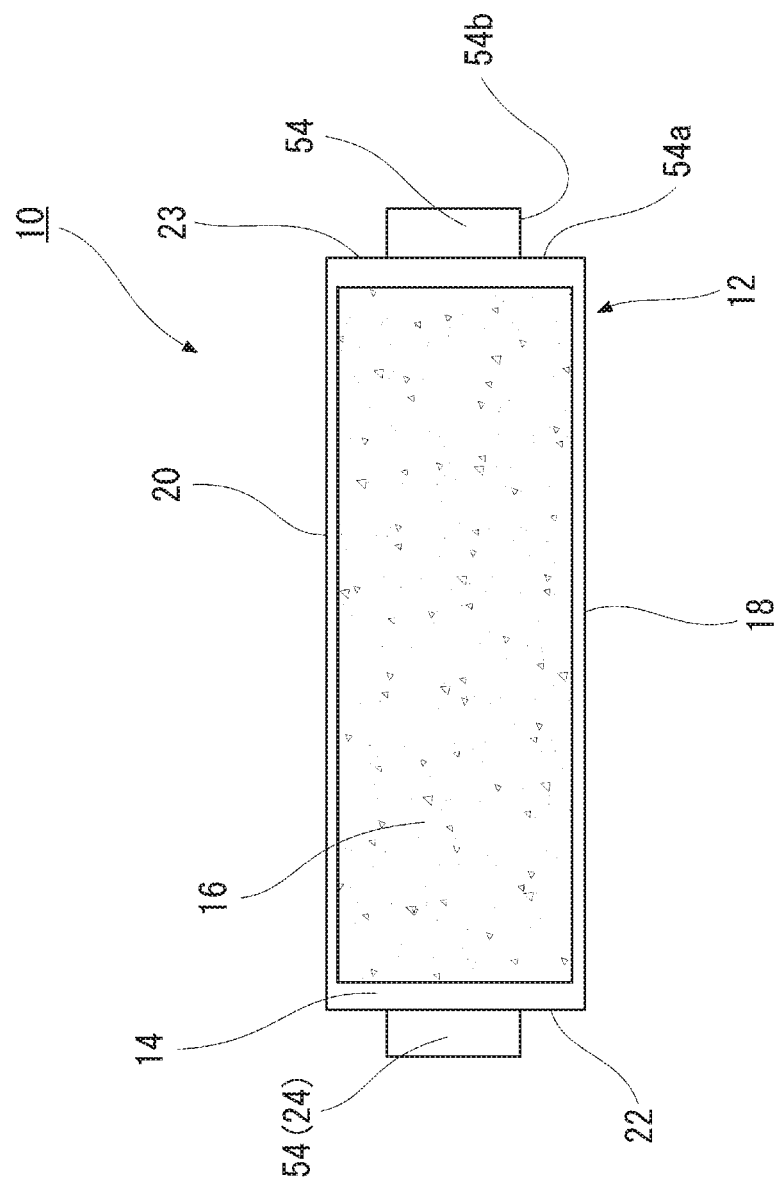

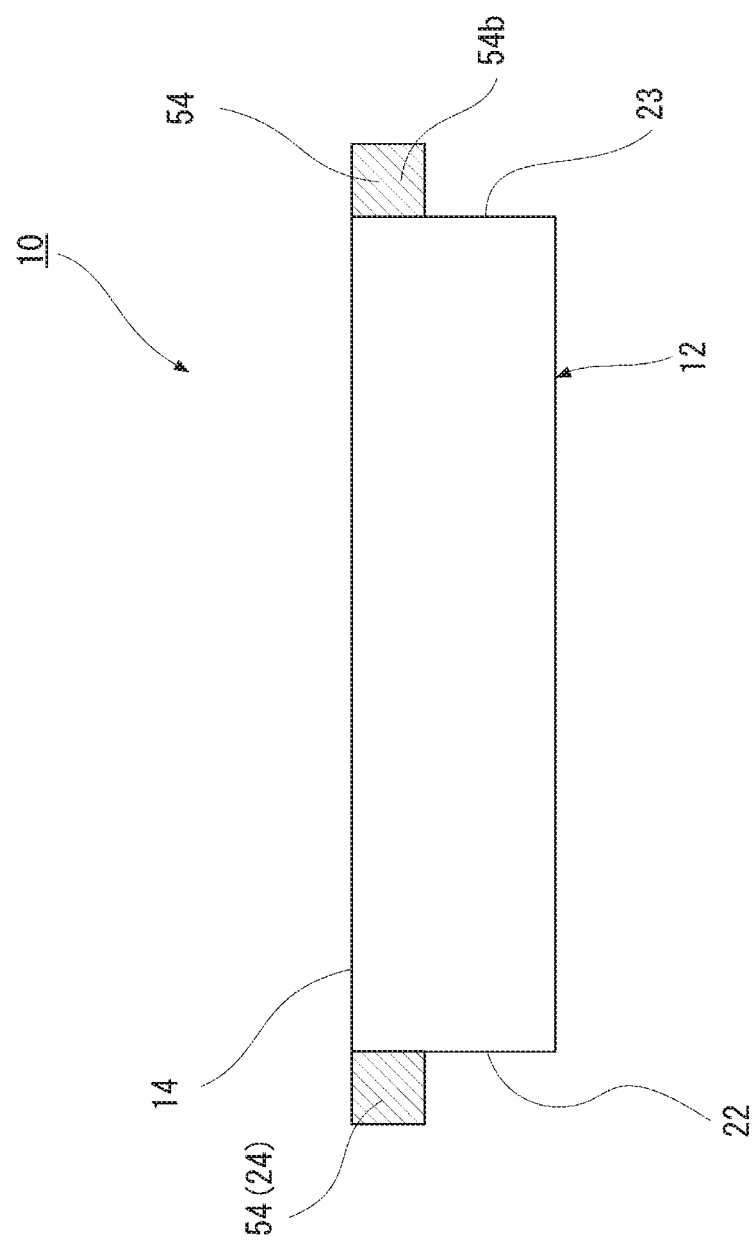
[Fig.14]

[Fig. 15]
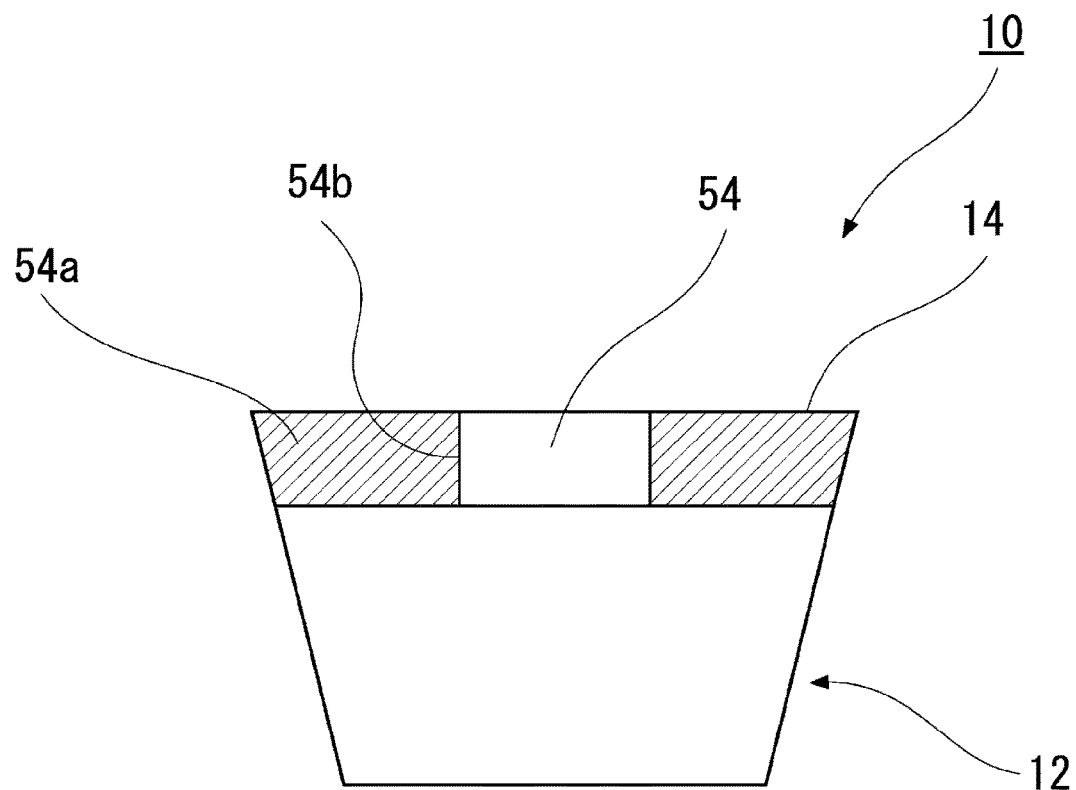

[Fig. 16]
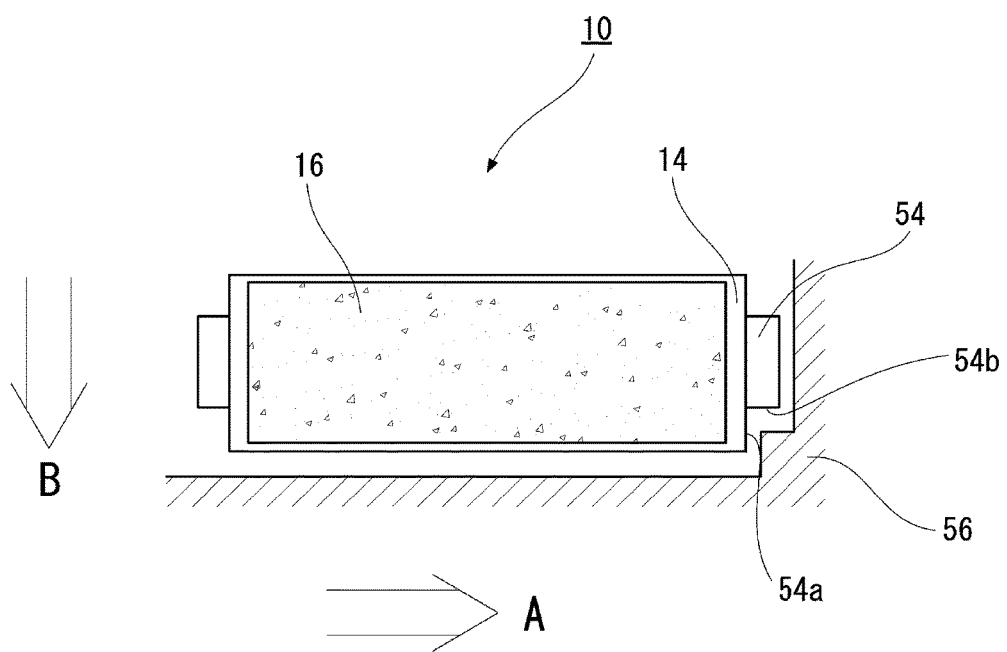

SENSOR CHIP FOR SPFS MEASUREMENT, SPFS MEASUREMENT METHOD USING SENSOR CHIP FOR SPFS MEASUREMENT, AND SPFS MEASUREMENT DEVICE EQUIPPED WITH SENSOR CHIP FOR SPFS MEASUREMENT

CROSS REFERENCE TO RELATED APPLICATIONS

The present U.S. patent application is a U.S. National Phase application under 35 USC 371 of International Application PCT/JP2012/083483 filed on Dec. 25, 2012. This application claims a priority under the Paris Convention of Japanese patent Application, No. 2011-283962 filed on Dec. 26, 2011, the entirety of which is incorporated herein by references.

TECHNICAL FIELD

The present invention relates to a sensor chip for SPFS measurement that is used for a surface plasmon-field enhanced fluorescence spectrometry device using a surface plasmon-filed enhanced fluorescence spectroscopy (SPFS; Surface Plasmon-field enhanced Fluorescence Spectroscopy) (hereinafter referred to simply as "SPFS") in the field of medical care or biotechnology, for example, and an SPFS measurement method using the sensor chip for SPFS measurement, and an SPFS measurement device equipped with the sensor chip for SPFS measurement.

BACKGROUND ART

Conventionally, in case of carrying out detection of a very small amount of a substance, various specimen detection devices with which such a substance can be detected by applying a physical phenomenon of the substance have been used.

One of such specimen detection devices is an SPFS device with which analyte detection can be carried out with a high precision on the basis of a principle of a surface plasmon-field enhanced fluorescence spectroscopy (SPFS) applying the surface plasmon resonance phenomenon.

The surface plasmon-field enhanced fluorescence spectroscopy (SPFS) is a method in which the evanescent wave generated by incoming of excitation light under the attenuated total reflection (ATR; attenuated total reflectance) conditions is resonated with surface plasmons on the surface of a metal thin film, and thereby, localized electric field, which is enhanced several tens to several hundreds of times, can be formed on the surface of the metal thin film; a fluorescent substance with which a captured analyte is conjugated (labeled) is set in this enhanced localized electric field; the fluorescence of the fluorescent substance is efficiently excited; and, by observing this fluorescence, a very slight amount or a very low concentration of an analyte is detected.

PRIOR ART DOCUMENTS

Patent Documents

[Patent Document 1] Japanese Patent No. 4689907

SUMMARY OF THE INVENTION

Problems to be Solved by the Invention

A sensor chip for SPFS measurement that is used for such an SPFS device has a dielectric member constituting a prism, and, on the top surface of this dielectric member, a metal thin film has been formed.

In a sensor chip for SPFS measurement having such arrangement, complicated matching of optical conditions is needed, and the storage stability of the optical properties and the quality of a sensor chip for SPFS measurement is an important requirement.

In particular, in case of a sensor chip for SPFS measurement which has a dielectric member made of a resin, there has been a problem that, depending on the environmental conditions, the variation of properties of the signal, the noise, the detection sensitivity and so on is large, and the quantitative property cannot be ensured.

Specifically, for example, there has been a problem that, in case where an environmental change, including the change in returning from the environment at the time of shipping and/or transporting (from −10° C. to 50° C.), storing in a refrigerator (4° C.), or storing in a freezer (−20° C.) to the temperature at which the sensor chip is actually used (from 20° C. to 37° C.), occurs, the quantitative property cannot be ensured.

In Patent Document 1 (Japanese Patent No. 4689907), it is proposed that, in a measurement chip which is used for a surface plasmon resonance device (SPR device) using the surface plasmon resonance (SPR) phenomenon, when injection molding of a substantially cup-shaped dielectric having a liquid pool part is carried out, a gate for introducing a resin (a resin inlet) is set in the bottom part of the dielectric and injection molding is carried out.

However, as described above, in case of the sensor chip for SPFS measurement, depending on the environmental conditions, the variation of properties of the signal, the noise, the detection sensitivity and so on is large, and the quantitative property cannot be ensured.

Accordingly, in case where a resin inlet is set in the bottom part of the dielectric and injection molding is carried out as shown in this Patent Document 1, as shown by the solid lines in the graph of FIG. 9 of Comparative Example 1 as described below, the sensor chip for SPFS measurement has a problem that, with regard to the S/N ratio which is a ratio of a signal to be detected to the background noise in the fluorescence measurement, the S/N ratios after leaving in the environment ("finalS/N") are decreased as compared to the initial S/N ratios ("iniS/N") and this hinders a highly precise and accurate SPFS measurement.

In addition, as shown by the dotted lines in the graph of FIG. 9 of Comparative Example 1, the sensor chip for SPFS measurement has a problem that the values of the CV, coefficient of variation, are not stable and this hinders a highly precise and accurate SPFS measurement.

In view of such circumstances, an object of the present invention is to provide a sensor chip for SPFS measurement, by which, irrespective of environmental conditions, the variation of properties of the signal, the noise, the detection sensitivity and so on is small, and the quantitative property can be ensured, and a highly precise and accurate SPFS measurement can be carried out, and an SPFS measurement method using the sensor chip for SPFS measurement, and an SPFS measurement device equipped with the sensor chip for SPFS measurement.

Means for Solving the Problems

The present invention has been made in order to solve the problems in the conventional techniques and accomplish the object as described above, and the sensor chip for SPFS measurement of the present invention is a sensor chip for SPFS measurement which has a dielectric member constituting a prism, said dielectric member having been produced by carrying out injection molding of a resin, characterized in that said sensor chip for SPFS measurement has been arranged such that a resin inlet is set on one side end surface of the dielectric member, said one side end surface intersecting with an excitation light incoming surface of said dielectric member, a metal thin film-formed surface of said dielectric member, and a reflected light outgoing surface through which a reflected light that comes in through said excitation light incoming surface and is reflected by the metal thin film-formed surface of said dielectric member goes out; and, when viewing from the metal thin film-formed surface side of said dielectric member and taking as b the distance of the side end surface position of said resin inlet to the position on said metal thin film-formed surface that is farthest from the side end surface position of said resin inlet, the center of a ligand immobilization part, which is a reaction part, is located in the area between the 3b/8 position and the 6b/8 position from the side end surface position of said resin inlet.

In addition, the SPFS measurement method of the present invention is characterized in that a sensor chip for SPFS measurement which has a dielectric member constituting a prism, said dielectric member having been produced by carrying out injection molding of a resin, wherein a resin inlet is set on one side end surface of the dielectric member, said one side end surface intersecting with an excitation light incoming surface of said dielectric member, a metal thin film-formed surface of said dielectric member, and a reflected light outgoing surface through which a reflected light that comes in through said excitation light incoming surface and is reflected by the metal thin film-formed surface of said dielectric member goes out, is used;

when viewing from the metal thin film-formed surface side of said dielectric member and taking as b the distance of the side end surface position of said resin inlet to the position on said metal thin film-formed surface that is farthest from the side end surface position of said resin inlet, an excitation light is irradiated to at least a portion of a metal thin film from the side where said dielectric member exists, said metal thin film having been formed on said dielectric member, said portion being located in the area between the 3b/8 position and the 6b/8 position from the side end surface position of said resin inlet; and fluorescence that is emitted by a fluorescent substance labeling an analyte immobilized by a ligand on said metal thin film is measured to calculate the amount of the analyte.

It is found that, by arranging like this, as shown by the solid lines in the graph of FIG. 5 of Example 1 as described below, with regard to the S/N ratio which is a ratio of a signal to be detected to the background noise in the fluorescence measurement, the S/N ratios after leaving in the environment ("finalS/N") are not decreased as compared to the initial S/N ratios ("iniS/N") and a highly precise and accurate SPFS measurement can be carried out.

In addition, it is found that, as shown by the dotted lines in the graph of FIG. 5 of Example 1 as described below, the values of the CV, coefficient of variation, are stable and a highly precise and accurate SPFS measurement can be carried out.

In other words, irrespective of environmental conditions, the variation of properties of the signal, the noise, the detection sensitivity and so on is small, and the quantitative property can be ensured, and a highly precise and accurate SPFS measurement can be carried out.

In addition, the present invention is characterized in that, on the metal thin film-formed surface of said dielectric member, a channel into which a specimen can be introduced has been formed.

By arranging like this, a channel into which a specimen can be introduced has been formed, and therefore, if a sample solution containing a specimen (an analyte) to be detected is made to flow in this channel, then the fluorescent substance with which the analyte captured in the vicinity of the metal thin film is conjugated (labeled) is efficiently excited, and, by observing this fluorescence, a very slight amount or a very low concentration of an analyte can be detected.

In addition, the present invention is characterized by having been arranged such that, in said channel, said ligand immobilization part has been formed, and the direction of the flow in said channel is parallel to the directions of said excitation light incoming surface and said reflected light outgoing surface of said dielectric member.

By arranging like this, the sample solution will flow in a direction parallel to the excitation light incoming surface and the reflected light outgoing surface of the dielectric member, and an analyte can be reliably captured in the ligand immobilization part having been formed in the channel.

Therefore, the fluorescent substance with which the analyte captured in the vicinity of the metal thin film is conjugated (labeled) is efficiently excited, and, by observing this fluorescence, a very slight amount or a very low concentration of an analyte can be detected.

In addition, the present invention is characterized in that, on said sensor chip for SPFS measurement, positioning and fixing parts to carry out positioning and fixing of the sensor chip for SPFS measurement in an SPFS measurement device with which detection is carried out are provided.

By arranging like this, using the positioning and fixing parts provided on the sensor chip for SPFS measurement, accurate positioning of the sensor chip for SPFS measurement can be carried out in an SPFS measurement device with which detection is carried out; therefore, accurate adjustment between the position of the center of the ligand immobilization part, which is a reaction part, and the position of the irradiated region can be carried out; and a highly precise and accurate SPFS measurement can be carried out.

In addition, the present invention is characterized in that said positioning and fixing parts have been formed in a channel lid member equipped on said dielectric member.

In addition, the present invention is characterized in that said positioning and fixing parts have been formed in said dielectric member.

In addition, the SPFS measurement device of the present invention is characterized by being equipped with the sensor chip for SPFS measurement according to any one of the preceding paragraphs.

Effects of the Invention

According to the present invention, irrespective of environmental conditions, the variation of properties of the signal, the noise, the detection sensitivity and so on is small, and the quantitative property can be ensured, and a highly precise and accurate SPFS measurement can be carried out.

BRIEF DESCRIPTION OF THE DRAWINGS

FIG. 1 is a perspective view of a sensor chip for SPFS measurement of the present invention.

FIG. 2 is a top view of the sensor chip for SPFS measurement of FIG. 1.

FIG. 3 is a schematic view illustrating the outline of the evaluation method that was carried out using the sensor chip for SPFS measurement of FIG. 1.

FIG. 4 is a partially enlarged cross-sectional view for explaining the outline of the sensor chip for SPFS measurement of FIG. 3.

FIG. 5 is a graph showing the results of the evaluation method.

FIG. 6 is a perspective view of a sensor chip for SPFS measurement of Comparative Example 1.

FIG. 7 is a top view of the sensor chip for SPFS measurement of FIG. 6.

FIG. 8 is a bottom view of the sensor chip for SPFS measurement of FIG. 6.

FIG. 9 is a graph showing the results of the evaluation method.

FIG. 10 is a top view of a sensor chip 10 for SPFS measurement of another example of the present invention.

FIG. 11 is a cross-sectional view taken along the line A-A in the sensor chip 10 for SPFS measurement of FIG. 10.

FIG. 12 is a cross-sectional view taken along the line B-B in the sensor chip 10 for SPFS measurement of FIG. 10.

FIG. 13 is a top view of a sensor chip 10 for SPFS measurement of yet another example of the present invention.

FIG. 14 is a front view of the sensor chip for SPFS measurement of FIG. 13.

FIG. 15 is a right side view of the sensor chip for SPFS measurement of FIG. 13.

FIG. 16 is a schematic top view for explaining a method for fixing the sensor chip for SPFS measurement of FIG. 13 to a sensor chip holder.

MODE FOR CARRYING OUT THE INVENTION

Embodiments (examples) of the present invention will now be described in more detail with reference to the drawings.

Example 1

FIG. 1 is a perspective view of a sensor chip for SPFS measurement of the present invention; FIG. 2 is a top view of the sensor chip for SPFS measurement of FIG. 1; FIG. 3 is a schematic view illustrating the outline of the evaluation method that was carried out using the sensor chip for SPFS measurement of FIG. 1; FIG. 4 is a partially enlarged cross-sectional view for explaining the outline of the sensor chip for SPFS measurement of FIG. 3; and FIG. 5 is a graph showing the results of the evaluation method.

As shown in FIGS. 1 to 2, the sensor chip 10 for SPFS measurement of this example is a sensor chip for SPFS measurement that is used for a surface plasmon-field enhanced fluorescence spectrometry device using a surface plasmon-field enhanced fluorescence spectroscopy (SPFS; Surface Plasmon-field enhanced Fluorescence Spectroscopy).

And, the sensor chip 10 for SPFS measurement has a dielectric member 12 constituting a dielectric member body and constituting a prism whose shape is a hexahedron having a cross section of a substantially trapezoidal shape (a shape of a truncated quadrangular pyramid), and the horizontal top surface of this dielectric member 12 constitutes a metal thin film-formed surface 14 on which a metal thin film 16 has been formed.

The sensor chip 10 for SPFS measurement is comprised of this dielectric member 12 and the metal thin film 16 which has been formed on the metal thin film-formed surface 14 of the dielectric member 12.

Further, as shown in FIG. 1, one side surface which is a lower part of the dielectric member 12 forms an excitation light incoming surface 18 through which an excitation light from a light source not shown comes in as indicated by the arrow in FIG. 1.

On the other hand, another side surface which is a lower part of the dielectric member 12 forms a reflected light outgoing surface 20 through which a reflected light reflected by the metal thin film 16 goes out as indicated by the arrow in FIG. 1.

With regard to the light which goes out through this reflected light outgoing surface 20, a light receiving means not shown that is set on the side of said another side surface which is a lower part of the dielectric member 12 receives the reflected light reflected by the metal thin film 16.

In this case, the material of the dielectric member 12 is at least formed from a material optically transparent to an excitation light, and, from the standpoint of providing a sensor chip 10 for SPFS measurement that is inexpensive and has an excellent handling property, is formed from a resin material by injection molding.

As the resin material from which the dielectric member 12 is formed, for example, a polyester such as polyethylene terephthalate (PET), polyethylene naphthalate and the like, a polyolefin such as polyethylene (PE), polypropylene (PP) and the like, a polycycloolefin such as a cycloolefin copolymer (COC), a cycloolefin polymer (COP) and the like, a vinyl resin such as polyvinyl chloride, polyvinylidene chloride and the like, polystyrene, polyether ether ketone (PEEK), polysulfone (PSF), polyether sulfone (PES), polycarbonate (PC), polyamide, polyimide, acrylic resin, triacetylcellulose (TAC), or the like can be used.

Then, as shown in FIGS. 1 to 2, a resin inlet (gate) 24 is set on one side end surface 22 of the dielectric member 12, said one side end surface 22 intersecting with the excitation light incoming surface 18 of the dielectric member 12, the metal thin film-formed surface 14 of the dielectric member 12, and the reflected light outgoing surface 20; and injection molding of a resin material is carried out to produce a dielectric member 12.

In this situation, the term "intersect" is intended to include not only cases of intersecting substantially perpendicularly, but also cases of intersecting at a certain angle, and is not limited.

(Evaluation Tests)

Using the sensor chip 10 for SPFS measurement of FIG. 1, the evaluation method as explained in FIG. 3 and FIG. 4 was carried out.

(1-1) Immobilization of Antigen Capturing Support:

Specifically, using a cycloolefin polymer (COP), a dielectric member 12 having dimensions of 25 mm length×8 mm width×3 mm height (Refractive Index: 1.52) was produced by injection molding.

Then, using a sputtering method, a metal thin film 16 having a thickness of 41 nm and comprised of gold was formed on a metal thin film-formed surface 14 of this dielectric member 12.

(1-2) Production of Channel:

As shown in FIG. 3, using an acrylic adhesive sheet (Thickness: 0.1 mm) which constitutes a channel wall 42 and wherein a channel groove of 3 mm width×23 mm length has been punched, a plate material (a lid) 13 having a thickness of 2 mm which constitutes a channel lid member 44 and is made of PMMA (polymethyl methacrylate resin) was bonded onto the surface of the sensor chip 10 for SPFS measurement to form a channel 46.

Then, as shown in FIG. 3, a laser light (Wavelength: 635 nm) was passed from a light source 26 through a wavelength separation filter (manufactured by Optical Coatings Japan) 28 and a polarizing plate 30; the light source 26 was fixed such that the angle of incidence of the laser light to the metal thin film 16 of the sensor chip 10 for SPFS measurement was an optimal angle; and thereafter, an excitation light by the light source 26 was irradiated to the sensor chip 10 for SPFS measurement.

FIG. 4 schematically illustrates a sensor chip for SPFS measurement. Evaluation of S/N ratios was carried out not in a system in which a dye was fixed on the gold film surface as shown in FIG. 4, but in a system in which the entire channel was filled with a buffer containing a dye.

And, via a 10× objective lens (manufactured by NIKON CORPORATION) as a light collecting means 32 and a wavelength separation filter (manufactured by Optical Coatings Japan) 34, fluorescence by a surface plasmon-field enhanced fluorescence spectroscopy was detected by using a photomultiplier PMT (manufactured by Hamamatsu Photonics K.K.) as a light receiving sensor 36.

Measurement conditions were as follows:
<Subjects to be Measured>

As a noise subject, a measurement buffer (a "Tris-Buffered Saline (TBS)" buffer) was made to flow in the channel.

As a signal subject, a dye containing buffer (a TBS buffer containing an "Alexa Fluor 647" reactive dye) was made to flow in the channel.
<Contents to be Evaluated>

Initial ("ini"): Without leaving a chip in the environment, measurement of a signal and the background noise was carried out.

After Leaving in Environment ("final"): After leaving a channel formed chip in the environment, i.e., after leaving in an environment of 60° C. and 80% by mass for 240 hours and thereafter leaving in a room temperature environment for 24 hours, measurement of a signal and the background noise was carried out.

As a result, when viewing from the metal thin film-formed surface 14 side of the dielectric member 12 and taking as b the distance of the side end surface position 12a of the resin inlet 24 to the position 18a on the metal thin film-formed surface 14 that is farthest from the side end surface position 12a of the resin inlet 24 as shown in FIG. 2, it was confirmed that, in the area between the 3b/8 position and the 6b/8 position from the side end surface position 12a of the resin inlet 24, the signal and the noise can be stably measured with or without leaving in the environment; and it was revealed that, when the center A of a ligand immobilization part 38 is set in the area between the 3b/8 position and the 6b/8 position, a highly precise and accurate SPFS measurement can be carried out (see the shaded area in FIG. 2).

That is to say, it is found that, as shown by the solid lines in the graph of FIG. 5, with regard to the S/N ratio which is a ratio of a signal to be detected to the background noise in the fluorescence measurement, the S/N ratios after leaving in the environment ("finalS/N") are not decreased as compared to the initial S/N ratios ("iniS/N") and a highly precise and accurate SPFS measurement can be carried out.

In addition, it is found that, as shown by the dotted lines in the graph of FIG. 5, the values of the CV, coefficient of variation, are stable and a highly precise and accurate SPFS measurement can be carried out.

In other words, it is found that, irrespective of environmental conditions, the variation of properties of the signal, the noise, the detection sensitivity and so on is small, and the quantitative property can be ensured, and a highly precise and accurate SPFS measurement can be carried out.

In the present invention, the material of the metal thin film 16 is not particularly limited, but is preferably comprised of at least one metal selected from the group consisting of gold, silver, aluminum, copper and platinum, more preferably comprised of gold, and may be comprised of an alloy of these metals.

These metals are suitable as a metal thin film 16, because they are stable to oxidization and electric field enhancement by surface plasmon light (compression wave) is increased as described below.

The method for forming a metal thin film 16 is not particularly limited, and examples thereof include, for example, a sputtering method, a vapor deposition method (such as a resistance heating vapor deposition method, an electron beam vapor deposition method and the like), an electrolytic plating method, an electroless plating method, and so on. It is desirable to preferably use a sputtering method or a vapor deposition method, since the thin film forming conditions thereof are easy to control.

Further, the thickness of a metal thin film 16 is not particularly limited, but preferably it is desirable that the thickness be within the ranges of: in case of gold, from 5 to 500 nm; in case of silver, from 5 to 500 nm; in case of aluminum, from 5 to 500 nm; in case of copper, from 5 to 500 nm; in case of platinum, from 5 to 500 nm; and in case of an alloy thereof, from 5 to 500 nm.

From the standpoint of the electric field enhancement effect, more preferably, it is desirable that the thickness be within the ranges of: in case of gold, from 20 to 70 nm; in case of silver, from 20 to 70 nm; in case of aluminum, from 10 to 50 nm; in case of copper, from 20 to 70 nm; in case of platinum, from 20 to 70 nm; and in case of an alloy thereof, from 10 to 70 nm.

If the thickness of a metal thin film 16 is within the above-described ranges, then surface plasmon light (compression wave) will be easily generated, therefore these ranges are suitable. In addition, as long as the metal thin film 16 has such a thickness, the shape thereof is not particularly limited.

A sensor chip 10 for SPFS measurement having been arranged like this is used as a sensor chip 10 for an SPFS measurement device.

A case where a sensor chip 10 for SPFS measurement is used for an SPFS device will now be described.

First, a solution containing a ligand that will specifically bind to an analyte to be detected is made to flow on a metal thin film 16 to immobilize the ligand onto the metal thin film 16, and thereafter, washing is carried out.

In the present invention, the term "sensor chip 10 for SPFS measurement" includes not only those in the state after carrying out immobilization of a ligand onto a metal thin film 16 like this, but also those in the state before carrying out immobilization of a ligand onto a metal thin film 16.

Thereafter, a sample solution containing an analyte conjugated (labeled) with a fluorescent substance is made to flow on the metal thin film 16 to allow it to specifically bind to the ligand on the metal thin film 16, and thereafter, washing is carried out.

A sample solution to be used here is a solution that has been prepared using a specimen, and examples thereof include, for example, those that have been obtained by mixing a specimen and a reagent(s) to carry out a treatment for making a fluorescent substance bind to an analyte contained in the specimen.

Examples of such a sample include blood, serum, plasma, urine, snivel, saliva, stool, coelomic fluid (spinal fluid, ascitic fluid, pleural fluid, or the like), and so on.

Examples of the analyte contained in the specimen include, for example, nucleic acids (DNAs, RNAs, polynucleotides, oligonucleotides, PNAs (peptide nucleic acids) and the like which may be either single-stranded or double-stranded, or nucleosides, nucleotides and modified molecules thereof), proteins (polypeptides, oligopeptides, and the like), amino acids (including modified amino acids), carbohydrates (oligosaccharides, polysaccharides, sugar chains, and the like), lipids, or modified molecules and complexes thereof, and so on. Specifically, the analyte contained in the specimen may be a carcinoembryonic antigen such as AFP ($\alpha$-fetoprotein), a tumor marker, a signal transducer, a hormone, or the like, and is not particularly limited.

Subsequently, as shown in FIG. 3, to the measurement point (irradiated region), i.e., the center A of a ligand immobilization part 38, and from a light source 26 set on the side of one side surface which is a lower part of a dielectric member 12, excitation light P1 is made to come in through an excitation light incoming surface 18 of the dielectric member 12 at an incidence angle of $\theta 1$ relative to the excitation light incoming surface 18 and refract, and the light is irradiated as excitation light P2 to a metal thin film 16 on the top surface of the dielectric member 12 at an incident angle of $\theta$ satisfying the total reflection conditions (at an incident angle of a certain angle (resonance angle)).

Then, reflected light P3 reflected by the metal thin film 16 is refracted on a reflected light outgoing surface 20 formed on another side surface which is a lower part of the dielectric member 12 at a certain angle $\theta 2$, and the light is received as reflected light P4 by a light receiving means not shown that is set on the side of said another side surface which is a lower part of the dielectric member 12. In this way, whether the angle is the predefined incident angle $\theta$ satisfying the total reflection conditions or not can be confirmed.

In other words, generation of surface plasmon light (compression wave) on the metal thin film 16 at an incident angle $\theta$ of a certain angle (resonance angle) can be found by discovering the point at which the signal of the reflected light P4 from the metal thin film 16 received by the light receiving means set on the side of the outgoing surface is changed (the amount of the light is decreased).

And, by this excitation light P2 irradiated on the metal thin film 16 on the top surface of the dielectric member 12, surface plasmon light (compression wave) is generated on the surface of the metal thin film 16; thereby, the photon amount which the excitation light P2 irradiated from the light source 26 has is increased several tens to several hundreds of times; and electric field enhancement effect of surface plasmon light is obtained.

By this electric field enhancement effect, a fluorescent substance with which an analyte captured by a ligand immobilized on the metal thin film 16 in the vicinity of the surface of the metal thin film 16 is conjugated (labeled) is efficiently excited, and, by observing this fluorescence, a very slight amount or a very low concentration of an analyte is detected.

In other words, in order to receive the fluorescence that is emitted by a fluorescent substance labeling the analyte, said analyte being captured by a ligand immobilized on the sensor chip 10 for SPFS measurement, a light receiving sensor 36, such as a photomultiplier (PMT), a CCD, or the like, is set above the sensor chip 10 for SPFS measurement.

Further, between the sensor chip 10 for SPFS measurement and the light receiving sensor 36, a light collecting means 32 to efficiently collect the light of the fluorescence, and a wavelength separation filter 34 to remove the lights other than the fluorescence and select only the fluorescence are set as shown in FIG. 3.

As a result, as described above, when viewing from the metal thin film-formed surface 14 side of the dielectric member 12 and taking as b the distance of the side end surface position 12a of the resin inlet 24 to the position 18a on the metal thin film-formed surface 14 that is farthest from the side end surface position 12a of the resin inlet 24 as shown in FIG. 2, if the center A of the ligand immobilization part 38, which is a reaction part, is located in the area between the 3b/8 position and the 6b/8 position from the side end surface position 12a of the resin inlet 24, then a highly precise and accurate SPFS measurement can be carried out.

Comparative Example 1

FIG. 6 is a perspective view of a sensor chip for SPFS measurement of Comparative Example 1; FIG. 7 is a top view of the sensor chip for SPFS measurement of FIG. 6; FIG. 8 is a bottom view of the sensor chip for SPFS measurement of FIG. 6; and FIG. 9 is a graph showing the results of the evaluation method.

A sensor chip 10 for SPFS measurement was produced in the same manner as in the evaluation test described above. However, as shown in FIG. 6 and FIG. 8, a resin inlet (gate) 24 is set in the bottom part 40 of a dielectric member 12.

Evaluation test was carried out in the same manner as the evaluation test of Example 1.

As a result, as shown by the solid lines in the graph of FIG. 9, in case of the sensor chip for SPFS measurement, a problem that, in case where the resin inlet 24 is set in the bottom part 40 of the dielectric member 12 and injection molding is carried out, with regard to the S/N ratio which is a ratio of an assay signal to be detected to an assay blank signal in the fluorescence measurement, the S/N ratios after leaving in the environment ("finalS/N") are decreased as compared to the initial S/N ratios ("iniS/N") and this hinders a highly precise and accurate SPFS measurement is found.

In addition, it is found that, as shown by the dotted lines in the graph of FIG. 9 of Comparative Example 1, the sensor chip for SPFS measurement has a problem that the values of the CV, coefficient of variation, are not stable and this hinders a highly precise and accurate SPFS measurement.

Example 2

FIG. 10 is a top view of a sensor chip 10 for SPFS measurement of another example of the present invention; FIG. 11 is a cross-sectional view taken along the line A-A in the sensor chip 10 for SPFS measurement of FIG. 10; and FIG. 12 is a cross-sectional view taken along the line B-B in the sensor chip 10 for SPFS measurement of FIG. 10.

Since the composition of the sensor chip 10 for SPFS measurement of this example is basically the same as that of the sensor chip 10 for SPFS measurement shown in FIGS. 1 to 5, the same composition member is numbered with the same reference number, and the detailed description thereof is omitted.

As shown in FIGS. 10 to 12, the sensor chip 10 for SPFS measurement of this example has, on a metal thin film-formed surface 14 of a dielectric member 12, a channel wall 42 constituted by a spacer, and has, on the top surface of this channel wall 42, a channel lid member 44.

Thereby, on the metal thin film-formed surface 14 of the dielectric member 12, a channel 46 into which a specimen can be introduced has been formed. In addition, in the channel lid member 44, two reagent inlets 48 apart from each other have been formed.

Further, on both side end parts 52 of one projected part 50 in the width direction of the channel lid member 44, concave-shaped positioning and fixing parts 54 to carry out positioning and fixing of the sensor chip 10 for SPFS measurement in an SPFS measurement device with which detection is carried out have been formed.

Moreover, in the sensor chip 10 for SPFS measurement of this example, since the center A of a ligand immobilization part 38, which is a reaction part, is located in the area between the 3b/8 position and the 6b/8 position from the side end surface position 12a of a resin inlet 24 as described above, the channel wall 42 and the channel lid member 44 have been formed at the positions that are shifted as a whole apart from the side end surface position 12a of the resin inlet 24 of the dielectric member 12.

Although positioning and fixing parts in a concave shape have been formed as a positioning and fixing part 54 in this example, the shape, number, setting position and the like of the positioning and fixing part 54 can be appropriately changed depending on the shape of the position fixing part on the side of the SPFS measurement device, for example, and a convex shape, a slit shape, or the like can be used.

By arranging like this, a channel 46 into which a specimen can be introduced has been formed, and therefore, if a sample solution containing a specimen (an analyte) to be detected is made to flow in this channel 46, then the fluorescent substance with which the analyte captured in the vicinity of the metal thin film is conjugated (labeled) is efficiently excited, and, by observing this fluorescence, a very slight amount or a very low concentration of an analyte can be detected.

In addition, using the positioning and fixing parts 54 provided on the sensor chip 10 for SPFS measurement, accurate positioning of the sensor chip 10 for SPFS measurement can be carried out in an SPFS measurement device with which detection is carried out; therefore, accurate adjustment between the position of the center of the ligand immobilization part 38, which is a reaction part, and the position of the irradiated region can be carried out; and a highly precise and accurate SPFS measurement can be carried out.

In this case, the direction of the flow in the channel 46 has been arranged so as to be parallel to the directions of the excitation light incoming surface 18 and the reflected light outgoing surface 20 of the dielectric member 12, as indicated by the arrow in FIG. 10. As long as the direction of the flow in the channel 46 is parallel to the directions of these surfaces, the direction may be either in a direction away from the side end surface position 12a of the resin inlet 24 of the dielectric member 12 or in the opposite direction.

By arranging like this, the sample solution will flow in a direction parallel to the excitation light incoming surface 18 and the reflected light outgoing surface 20 of the dielectric member 12, and an analyte can be reliably captured in the ligand immobilization part 38 having been formed in the channel 46.

Therefore, the fluorescent substance with which the analyte captured in the vicinity of the metal thin film 16 is conjugated (labeled) is efficiently excited, and, by observing this fluorescence, a very slight amount or a very low concentration of an analyte can be detected.

Example 3

FIG. 13 is a top view of a sensor chip 10 for SPFS measurement of yet another example of the present invention; FIG. 14 is a front view of the sensor chip for SPFS measurement of FIG. 13; and FIG. 15 is a right side view of the sensor chip 10 for SPFS measurement of FIG. 13.

Since the composition of the sensor chip 10 for SPFS measurement of this example is basically the same as that of the sensor chips 10 for SPFS measurement shown in FIGS. 1 to 12, the same composition member is numbered with the same reference number, and the detailed description thereof is omitted.

In the above-described Example 2, on both side end parts 52 of one projected part 50 in the width direction of the channel lid member 44, concave-shaped positioning and fixing parts 54 have been formed. On the other hand, in the sensor chip 10 for SPFS measurement of this example, as shown in FIGS. 13 to 15, on both of the side end surface 22 and the side end surface 23 of a dielectric member 12, convex-shaped positioning and fixing parts 54 have been formed.

In this example, by carrying out injection molding of a resin material, the positioning and fixing parts 54 can be molded integrally with the dielectric member 12.

One of the positioning and fixing parts 54 may be a resin inlet 24.

A sensor chip 10 for SPFS measurement comprised of a dielectric member 12 having positioning and fixing parts 54 in this way is used after carrying out positioning and fixing thereof to a sensor chip holder fixed in an SPFS measurement device.

Specifically, as shown in FIG. 16, in a state where a sensor chip 10 is mounted on a sensor chip holder 56 fixed in an SPFS measurement device, the sensor chip is urged in the A direction. Then, a reference surface 54a of the positioning and fixing part 54 is brought into contact with the internal surface of the sensor chip holder 56, and thereby, positioning thereof in the A direction is done.

Further, the sensor chip is urged in the B direction, and then, a reference surface 54b of the positioning and fixing part 54 is brought into contact with the internal surface of the sensor chip holder 56, and thereby, positioning thereof in the B direction is done.

Although positioning and fixing parts in a convex shape have been formed as a positioning and fixing part 54 in this example, the shape, number, setting position and the like of the positioning and fixing part 54 can be appropriately changed depending on the shape of the sensor chip holder 56 on the side of the SPFS measurement device, for example, and a concave shape, a slit shape, or the like can be used.

By arranging like this, using the positioning and fixing parts 54 molded integrally with the dielectric member 12, accurate positioning of the sensor chip 10 for SPFS measurement can be carried out in an SPFS measurement device with which detection is carried out; therefore, accurate adjustment between the position of the center of the ligand immobilization part 38, which is a reaction part, and the position of the irradiated region can be carried out; and a highly precise and accurate SPFS measurement can be carried out.

Preferred embodiments of the present invention have been described above, but the present invention is not limited thereto. For example, although, in the above examples, the shape of the dielectric member 12 constituting a prism is a hexahedron having a cross section of a substantially trapezoidal shape (a shape of a truncated quadrangular pyramid), the shape of the dielectric member 12 is not particularly limited, and may be changed to a shape of a triangular prism having a cross section of a triangle, for example. Like this, various modifications can be made within a scope not departing from the object of the present invention.

INDUSTRIAL APPLICABILITY

The present invention can be applied to a sensor chip for SPFS measurement that is used for a surface plasmon-field enhanced fluorescence spectrometry device using a surface plasmon-field enhanced fluorescence spectroscopy (SPFS; Surface Plasmon-field enhanced Fluorescence Spectroscopy) (hereinafter referred to simply as "SPFS") in the field of medical care or biotechnology, for example, and an SPFS measurement method using the sensor chip for SPFS measurement, and an SPFS measurement device equipped with the sensor chip for SPFS measurement.

The invention claimed is:
1. A sensor chip for SPFS (Surface Plasmon-field enhanced Fluorescence Spectroscopy) measurement which has a dielectric member constituting a prism, said dielectric member having been produced by carrying out injection molding of a resin, characterized in that said sensor chip for SPFS measurement has been arranged such that
a resin inlet is set on one side end surface of the dielectric member, said one side end surface intersecting with an excitation light incoming surface of said dielectric member, a metal thin film-formed surface of said dielectric member, and a reflected light outgoing surface through which a reflected light that comes in through said excitation light incoming surface and is reflected by the metal thin film-formed surface of said dielectric member goes out; and,
when viewing from the metal thin film-formed surface side of said dielectric member and taking as b the distance of the side end surface position of said resin inlet to the end surface position of the metal thin film-formed surface that does not have the resin inlet,
the center of a ligand immobilization part, which is a reaction part, is located on the metal thin film in the area between the 3b/8 position and the 6b/8 position from the side end surface position of said resin inlet;
on said sensor chip for SPFS measurement, positioning and fixing parts to carry out positioning and fixing of the sensor chip for SPFS measurement in an SPFS measurement device with which detection is carried out are provided;
said positioning and fixing parts have been formed in said dielectric member; and
wherein the positioning and fixing part is the resin inlet.
2. The sensor chip for SPFS measurement according to claim 1, characterized in that, on the metal thin film-formed surface of said dielectric member, a channel into which a specimen can be introduced has been formed.
3. The sensor chip for SPFS measurement according to claim 2, characterized by having been arranged such that,
in said channel, said ligand immobilization part has been formed, and
the direction of the flow in said channel is parallel to the directions of said excitation light incoming surface and said reflected light outgoing surface of said dielectric member.

4. The sensor chip for SPFS measurement according to claim 1, characterized in that said positioning and fixing parts have been formed in a channel lid member equipped on said dielectric member.
5. An SPFS measurement device, characterized by being equipped with the sensor chip for SPFS measurement according to claim 1,
wherein the SPFS measurement device comprises a light source for applying an excitation light to the metal thin film through the excitation light incoming surface of the dielectric member constituting the sensor chip for SPFS measurement, and a light receiving sensor for receiving a fluorescence excited at a position of the ligand immobilization part on the metal thin film.
6. A SPFS (Surface Plasmon-field enhanced Fluorescence Spectroscopy) measurement method, characterized in that
a sensor chip for SPFS measurement which has a dielectric member constituting a prism, said dielectric member having been produced by carrying out injection molding of a resin,
wherein a resin inlet is set on one side end surface of the dielectric member, said one side end surface intersecting with an excitation light incoming surface of said dielectric member, a metal thin film-formed surface of said dielectric member, and a reflected light outgoing surface through which a reflected light that comes in through said excitation light incoming surface and is reflected by the metal thin film-formed surface of said dielectric member goes out,
is used;
a sample solution containing an analyte conjugated with a fluorescent substance is flowed on the metal thin film;
when viewing from the metal thin film-formed surface side of said dielectric member and taking as b the distance of the side end surface position of said resin inlet to the end surface position of the metal thin film-formed surface that does not have the resin inlet,
an excitation light is irradiated to at least a portion of a metal thin film through the excitation light incoming surface of said dielectric member, said metal thin film having been formed on said dielectric member, said portion being located on the metal thin film in the area between the 3b/8 position and the 6b/8 position from the side end surface position of said resin inlet;
fluorescence that is emitted by the fluorescent substance labeling the analyte immobilized by a ligand on said metal thin film is received to calculate the amount of the analyte for the SPFS measurement;
on said sensor chip for SPFS measurement, positioning and fixing parts to carry out positioning and fixing of the sensor chip for SPFS measurement in an SPFS measurement device with which detection is carried out are provided;
said positioning and fixing parts have been formed in said dielectric member; and
wherein the positioning and fixing part is the resin inlet.
7. The SPFS measurement method according to claim 6, characterized in that, on the metal thin film-formed surface of said dielectric member, a channel into which a specimen can be introduced has been formed.
8. The SPFS measurement method according to claim 7, characterized by having been arranged such that,
in said channel, a ligand immobilization part has been formed, and the direction of the flow in said channel is parallel to the directions of said excitation light incoming surface and said reflected light outgoing surface of said dielectric member.

9. The SPFS measurement method according to claim 7, characterized in that, on said sensor chip for SPFS measurement, positioning and fixing parts to carry out positioning and fixing of the sensor chip for SPFS measurement in an SPFS measurement device with which detection is carried out are provided.

10. The SPFS measurement method according to claim 8, characterized in that, on said sensor chip for SPFS measurement, positioning and fixing parts to carry out positioning and fixing of the sensor chip for SPFS measurement in an SPFS measurement device with which detection is carried out are provided.

11. The SPFS measurement method according to claim 6, characterized in that said positioning and fixing parts have been formed in a channel lid member equipped on said dielectric member.

\* \* \* \* \*